(12) United States Patent
Kouno et al.

(10) Patent No.: US 6,525,218 B2
(45) Date of Patent: Feb. 25, 2003

(54) PROCESS FOR PRODUCING SORBIC ACID

(75) Inventors: Mitsuhiro Kouno, Arai (JP); Tadayuki Mitani, Himeji (JP); Noboru Kamei, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/922,857

(22) Filed: Aug. 7, 2001

(65) Prior Publication Data

US 2002/0022745 A1 Feb. 21, 2002

(30) Foreign Application Priority Data

Aug. 8, 2000 (JP) .......................................... 2000-240216

(51) Int. Cl.$^7$ .............................................. C07C 57/10
(52) U.S. Cl. ...................................................... 562/601
(58) Field of Search .......................................... 562/601

(56) References Cited

U.S. PATENT DOCUMENTS 4,639,294 A * 1/1987 Kamei et al. ................... 203/88

FOREIGN PATENT DOCUMENTS

| EP | 1 035 149 A1 | 9/2000 |
|---|---|---|
| JP | 44-26646 | 11/1969 |
| JP | 54-163516 | 12/1979 |
| JP | 10-95745 * | 4/1998 |

OTHER PUBLICATIONS

Database WPI, Section Ch, Week 199750 Derwent Publications Ltd., London Gb; Class D13, AN 1997–539687 XP002183544 & JP 09 227447 A (Nippon Synthetic Chem Ind Co), Sep. 2, 1997 (09–02–1997) *abstract*.
Kamei et al., Patent Abstracts of Japan, 2000–103846, published Apr. 11, 2000.

* cited by examiner

*Primary Examiner*—Richard L. Raymond
*Assistant Examiner*—Zachary C. Tucker
(74) *Attorney, Agent, or Firm*—Birch, Stewart, Kolasch & Birch, LLP

(57) ABSTRACT

A process produces sorbic acid by hydrolyzing a polyester with an aqueous hydrochloric acid solution having a concentration of 15% by weight or less under the application of pressure or at a temperature of 100° C. or higher, which polyester is obtained by reaction between crotonaldehyde and ketene. In this process, the polyester may be hydrolyzed with a 3 to 10% by weight aqueous hydrochloric acid solution at a temperature of from 115° C. to 140° C. A reaction mixture after hydrolysis of the polyester may be subjected to solid-liquid separation and the resulting filtrate may be recycled and reused in the hydrolysis reaction of the polyester. This process can significantly reduce the amount of tar formed during decomposition of the polyester, can produce sorbic acid in a high yield, and can reduce the load on the treatment of waste filtrates formed during purification operation.

7 Claims, No Drawings

PROCESS FOR PRODUCING SORBIC ACID

BACKGROUND OF THE INVENTION

1. Field of the Invention

The present invention relates to a process for efficiently producing sorbic acid from a polyester, which polyester is a polymerization reaction product between crotonaldehyde and ketene. The product sorbic acid is useful, for example, as a food additive.

2. Description of the Related Art

Sorbic acid and its salts have antiseptic and antimicrobial activities and are substantially nontoxic to the human body in normal concentrations in practical use. These compounds are therefore useful as food additives. Of a variety of known processes for producing sorbic acid, a commercially important pathway is. a process of polymerizing crotonaldehyde and ketene to form an intermediate polyester, decomposing the polyester to yield a crude sorbic acid, and subjecting the crude sorbic acid to a variety of purification operations to thereby yield a purified sorbic acid. The polyester is decomposed, for example, with hydrochloric acid, with an alkali, or by heat. Sorbic acid obtained by these techniques contains a variety of colored substances, tarry substances and other impurities and is subjected to purification operations.

For example, Japanese Examined Patent Application Publication No. 44-26646 discloses a process for producing sorbic acid. In this process, a polyester obtained by a reaction between crotonaldehyde and ketene is decomposed with hydrochloric acid having a concentration of equal to or more than 35% by weight at a temperature equal to or higher than room temperature (ordinary temperature) and less than or equal to around the boiling point of the hydrochloric acid used, followed by cooling and filtrating the resulting reaction mixture to separate a crude sorbic acid, and the crude sorbic acid is rinsed with water, is then put into water and is dissolved by heating, followed by addition of activated carbon and boiling, the reaction mixture is filtrated before it gets cold, and the filtrate is gradually cooled to thereby yield a crystalline sorbic acid.

Japanese Unexamined Patent Application Publication No. 54-163516 discloses a process for producing a sorbic acid. In this process, a polyester obtained from ketene and crotonaldehyde is decomposed with hydrochloric acid in the presence of, for example, a urea compound, the resulting decomposition reaction mixture is filtrated and rinsed to yield a crude sorbic acid, followed by addition of an aqueous sodium hydroxide solution to the crude sorbic acid to thereby yield an aqueous sodium sorbate solution, the aqueous sodium sorbate solution is treated with activated carbon, is neutralized and is cooled to thereby crystallize sorbic acid.

However, these processes invite loss of sorbic acid due to the formation of tar during decomposition of the polyester or invite loss of sorbic acid due to dissolution of sorbic acid into a filtrate separated from the crystal of sorbic acid by solid-liquid separation. Additionally, in these processes, the reaction mixture must be subjected to solid-liquid separation including dissolution in a treatment solvent and recrystallization during purification operations in order to remove the tar contents and these operations invite further loss of sorbic acid to thereby markedly decrease the yield of sorbic acid. Furthermore, the resulting filtrates exhibit a very high BOD (biochemical oxygen demand) and must be treated to reduce the BOD, and such treatments require a great deal of facilities and costs.

SUMMARY OF THE INVENTION

Accordingly, an object of the present invention is to provide a process for producing sorbic acid, which process can significantly reduce the amount of tar formed during decomposition of the polyester, can produce sorbic acid in a high yield, and can reduce the load on the treatment of waste filtrates formed during purification operations.

After intensive investigations to achieve the above objects focusing attention on the hydrolysis operation of the polyester with hydrochloric acid among a series of production operations for sorbic acid, the present inventors have found that the by-production of tar can be markedly inhibited by specifying ranges of the concentration of hydrochloric acid and decomposition pressure or decomposition temperature. The present invention has been accomplished based on these findings.

Specifically, the present invention provides, in an aspect, a process for producing sorbic acid. This process includes the step of hydrolyzing a polyester with aqueous hydrochloric acid solution having a concentration of less than or equal to 15% by weight under the application of pressure, which polyester is a reaction product between crotonaldehyde and ketene. In this process, the polyester may be hydrolyzed under the application of pressure (under a load) of equal to or greater than 0.05 MPa.

In another aspect, the present invention provides a process for producing sorbic acid, which process includes the step of hydrolyzing a polyester with aqueous hydrochloric acid solution having a concentration of less than or equal to 15% by weight at a temperature of equal to or higher than 100° C., which polyester is a reaction product between crotonaldehyde and ketene.

In these production processes, the polyester may be hydrolyzed with an aqueous hydrochloric acid having a concentration of from 3 to 10% by weight at a temperature of from 115° C. to 140° C. Additionally, the polyester may be hydrolyzed in such a manner that a molten sorbic acid is dispersed in a reaction mixture without layer separation. A filtrate obtained by solid-liquid separation of a reaction mixture after the hydrolysis of the polyester may be recycled and reused in the hydrolysis reaction of the polyester as part or all of the aqueous hydrochloric acid solution.

The phrase "under the application of pressure" as used herein also includes a condition in which a reaction pressure is increased by hermetically sealing a reaction system and heating the reaction system.

DESCRIPTION OF THE PREFERRED EMBODIMENTS

A main feature of processes for producing sorbic acid according to the present invention is that a polyester is decomposed in a reaction system under the application of pressure (under a load) or at a temperature of equal to or higher than 100° C. with the use of aqueous hydrochloric acid solution having a relatively low concentration (i.e., a concentration of less than or equal to 15% by weight).

When a reaction is performed at a pressure of less than or equal to normal pressure (atmospheric pressure) at temperatures of lower than 100° C. and the concentration of hydrochloric acid is low, it takes long for the polyester supplied to the reaction system to completely decompose, and sorbic acid formed during the early stage of reaction is converted into tar. In contrast, when the reaction is performed under the application of pressure (under a load) or at a temperature of equal to or higher than 100° C. and the concentration of hydrochloric acid exceeds 15% by weight, the decomposition reaction itself rapidly proceeds but sorbic acid formed by decomposition is also rapidly converted into black tar.

This is probably because hydrochloric acid or free chlorine significantly affects the conversion of sorbic acid into tar and the inhibition of the conversion. Specifically, it is speculated that sorbic acid can only stably exist at predetermined temperatures within an appropriate range of hydrochloric acid concentration, and if the concentration of hydrochloric acid is less than or exceeds the appropriate range, sorbic acid is rapidly converted into tar. If the reaction is performed using water alone in the absence of hydrochloric acid, a 1,4-addition polymer (yellow tar) is formed.

In the conventional decomposition processes using hydrochloric acid, bearing operation at temperatures lower than 100° C. in mind, a concentrated hydrochloric acid is used at an early stage of reaction to thereby rapidly decompose most of the polyester, and an aging operation is then performed by lowering the temperature or decreasing the concentration of hydrochloric acid. These processes pay attention to the decomposition rate of the polyester alone without significant consideration of the influence of hydrochloric acid on conversion of the decomposition product sorbic acid into tar.

According to the present invention, the reaction is performed under the application of pressure or at temperatures equal to or higher than 100° C. using hydrochloric acid having a relatively low concentration of less than or equal to 15% by weight. The polyester is therefore decomposed at a practical rate and sorbic acid is converted into tar at a very low rate. Consequently, sorbic acid can be efficiently produced and purification operations and after-treatment operations can be simplified.

Any polyesters can be used in the decomposition with hydrochloric acid as far as they are synthetically obtained by known or conventional methods. Generally, such polyesters are commercially produced by the reaction of crotonaldehyde with ketene in the presence of a catalyst. Such catalysts include, but are not limited to, elementary substances or compounds of manganese, cobalt, nickel, zinc, cadmium, and other transition metals; and pyridine, picoline, and other nitrogen-containing basic substances. The compounds of transition metals include, for example, oxides; acetates, isobutyrates, isovalerates, and other organic acid salts; sulfates, nitrates, and other inorganic acid salts; chlorides and other halides; and acetylacetone complexes and other complex salts or complexes. Each of these catalysts can be used alone or in combination. The amount of the catalyst depends on the type of the catalyst and is generally from about 0.1 to about 10% by weight relative to ketene. A reaction temperature in the reaction of crotonaldehyde with ketene is, for example, from about 20° C. to about 100° C. and preferably from about 25° C. to about 80° C. A reaction mixture containing the polyester obtained by the reaction of crotonaldehyde with ketene is generally subjected to distillation to thereby remove unreacted crotonaldehyde and low-boiling impurities and is then subjected to the decomposition reaction with hydrochloric acid.

According to the present invention, the polyester is decomposed with hydrochloric acid under the application of pressure or at temperatures equal to or higher than 100° C., and the reaction is generally performed in a hermetically closed system. For example, the polyester and aqueous hydrochloric acid solution are placed in a pressure-resistant, acid-resistant container, the container is sealed and is raised in temperature to a predetermined temperature while stirring the charge to thereby decompose the polyester. Pressurization such as by gas injection is not necessary if ebullition (boiling) of the contents can be prevented by sealing. The ratio of the polyester to aqueous hydrochloric acid solution is not specifically limited.

When the polyester is decomposed at temperatures equal to or higher than 115° C., the resulting sorbic acid is liquid and is separated from and floats on the aqueous hydrochloric acid solution when the reactor is allowed to stand. Such molten sorbic acid in little contact with hydrochloric acid is readily converted into tar. Consequently, the reaction is preferably performed, for example, with stirring by a stirrer or other stirring means so that the molten sorbic acid is completely dispersed in the aqueous hydrochloric acid solution (reaction mixture) without layer separation.

The polyester is preferably hydrolyzed at a temperature of from about 115° C. to about 140° C. and is typically preferably hydrolyzed under the application of pressure at a gauge pressure of equal to or greater than 0.05 MPa (e.g., from about 0.05 to about 1 MPa), i.e., at an absolute pressure of equal to or greater than 0.15 MPa (e.g., from about 0.15 to about 1.1 MPa).

When the decomposition of the polyester surely completes, a subsequent cooling operation is generally performed without delay. The cooling technique is not specifically limited. For example, the reaction mixture can be quenched by adding cold aqueous hydrochloric acid solution having a concentration equal to or lower than the hydrogen chloride (HCl) concentration of the reaction system.

The precipitated crystal in a decomposition reaction mixture as a result of cooling is subjected to solid-liquid separation such as filtration or centrifugal separation to thereby yield sorbic acid. The above-prepared sorbic acid is further subjected to a simple purification operation such as rinsing with an appropriate amount of water to thereby yield sorbic acid having a higher purity and more satisfactory hue quality (color quality) than crude sorbic acid obtained by conventional decomposition processes with hydrochloric acid.

The crude sorbic acid obtained by conventional decomposition processes with hydrochloric acid requires two purification operations including dissolution and recrystallization after this operation in order to attain sufficient quality as a product. In contrast, the sorbic acid obtained by the invented process can attain sufficient quality after at most one purification operation. Accordingly, the invented process can avoid the loss of sorbic acid into a filtrate during purification operation and do not require the treatment of the filtrate itself and is advantageous in yield of product and in reduction of cost for waste filtrate treatment.

Additionally, the filtrate separated by filtration after decomposition of the polyester is very slightly colored by tar and can be recycled and reused in decomposition of the polyester without any problem, where necessary after adjustment of the concentration with fresh aqueous hydrochloric acid solution.

If the polyester is decomposed at temperatures equal to or higher than 100° C. in the absence of hydrochloric acid, the polyester is decomposed at a very low rate and the formed sorbic acid is polymerized and is converted into tar, thus deteriorating the yield. In contrast, in the presence of excess hydrochloric acid, the polyester is rapidly decomposed but the formed sorbic acid is also rapidly converted into tar, thus decreasing the yield upon the completion of the decomposition. As thus described, it is important to carefully control the pressure or temperature and the concentration of hydrochloric acid in order to decompose the polyester with hydrochloric acid in a high yield under the application of pressure or at temperatures equal to or higher than 100° C. The concentration of aqueous hydrochloric acid solution (the concentration of hydrogen chloride) for use in the reaction is preferably from about 0.5 to about 15% by weight and more preferably from about 3 to about 10% by weight.

The invented processes can produce sorbic acid in a high yield and can simplify a purification operation for the removal of tar and are very useful. The product sorbic acid and its salts (e.g., potassium sorbate) can be used as preservatives for foods such as fish pastes, butters, cheeses, bean pastes, and preserves.

Advantages

The invented processes can produce sorbic acid in a high yield, can simplify the purification operation and can markedly reduce the load on treatment of the resulting filtrate. This is probably because the polyester is decomposed at a high pressure or at high temperatures and the concentration of hydrochloric acid is allowed to be optimum for the inhibition of conversion of sorbic acid into tar.

The present invention will be illustrated in further detail with reference to several examples and a comparative example below, which are not intended to limit the scope of the invention.

EXAMPLE 1

In a pressure-resistant, acid-resistant glass reactor, 7 g of a polyester obtained by reaction between crotonaldehyde and ketene and 100 g of a 7% by weight aqueous hydrochloric acid solution were placed, the reactor was sealed and was heated to 130° C. in an oil bath with stirring by a magnetic stirrer, to thereby pressurize the reaction system. The reactor was heated until the polyester was completely decomposed, the reactor was taken out from the bath and was cooled by dissipation of heat to thereby precipitate crystalline sorbic acid. The reactor was opened and an appropriate amount of acetone was placed therein, followed by dissolution of all the contents in acetone and recovery of the resulting solution. The recovered solution was analyzed by gas chromatography and the amount of the recovered sorbic acid was calculated from the obtained sorbic acid concentration to thereby find the yield of sorbic acid based on the used polyester was 94.0%.

EXAMPLE 2

Sorbic acid-was produced in the same manner as in Example 1, except that a 10% by weight aqueous hydrochloric acid solution was used and that the maximum temperature in temperature elevation operation was set at 120° C. The calculated yield of sorbic acid based on the used polyester was 92.0%.

EXAMPLE 3

Sorbic acid was produced in the same manner as in Example 1, except that 80 g of the aqueous hydrochloric acid solution and 20 g of the polyester were used. The calculated yield of sorbic acid based on the used polyester was 87.0%.

COMPARATIVE EXAMPLE 1

Sorbic acid was produced in the same manner as in Example 1, except that 80 g of a 33% by weight aqueous hydrochloric acid solution and 20 g of the polyester were used, that the maximum temperature in temperature elevation operation was set at 80° C. and that the reaction was performed at normal atmospheric pressure. The calculated yield of sorbic acid based on the used polyester was 80.0%.

Other embodiments and variations will be obvious to those skilled in the art, and this invention is not to be limited to the specific matters stated above.

What is claimed is:

1. A process for producing sorbic acid, said process comprising the step of hydrolyzing a polyester, which is a reaction product between crotonaldehyde and ketene, with aqueous hydrochloric acid solution having a concentration of from 3 to 10% by weight under a pressure greater than atmospheric pressure.

2. The process according to claim 1, wherein said polyester is hydrolyzed under a pressure of equal to or higher than 0.15 MPa as an absolute pressure.

3. A process for producing sorbic acid, said process comprising the step of hydrolyzing a polyester, which is a reaction product between crotonaldehyde and ketene, with aqueous hydrochloric acid solution having a concentration of less than or equal to 15% by weight at a temperature equal to or higher than 115° C.

4. The process according to any one of claims 1 to 3, wherein said polyester is hydrolyzed with aqueous hydrochloric acid solution having a concentration of from 3 to 10% by weight at a temperature of from 115° to 140° C.

5. The process according to any one of claims 1 to 3, wherein a reaction mixture after the hydrolysis of said polyester is subjected to solid-liquid separation, and the resulting filtrate is recycled and reused in the hydrolysis reaction of the polyester.

6. A process for producing sorbic acid, said process comprising the step of hydrolyzing a polyester, which is a reaction product between crotonaldehyde and ketene, with aqueous hydrochloric acid solution having a concentration of less than or equal to 15% by weight under a pressure greater than atmospheric pressure to yield a molten sorbic acid in such a manner that the resulting molten sorbic acid is dispersed in a reaction mixture without layer separation.

7. A process for producing sorbic acid, said process comprising the step of hydrolyzing a polyester, which is a reaction product between crotonaldehyde and ketene, with aqueous hydrochloric acid solution having a concentration of less than or equal to 15% by weight at a temperature equal to or higher than 115° C. to yield a molten sorbic acid in such a manner that the resulting molten sorbic acid is dispersed in a reaction mixture without layer separation.

* * * * *